United States Patent [19]
Hsia et al.

[11] Patent Number: 6,013,163
[45] Date of Patent: Jan. 11, 2000

[54] PROBE FOR DETECTION OF THE CONCENTRATION OF VARIOUS ELEMENTS IN MOLTEN METAL

[75] Inventors: Chungwei Hsia, Monroeville; Harry Kozer Harbaugh, Murrysville; Kenneth Dwight Powers, Derry Township, Westmoreland County, all of Pa.

[73] Assignee: USX Corporation, Pittsburgh, Pa.

[21] Appl. No.: 08/896,474

[22] Filed: Jul. 18, 1997

[51] Int. Cl.[7] .................................................. G01N 27/411
[52] U.S. Cl. ........................ 204/422; 204/423; 205/783.5
[58] Field of Search ..................................... 204/421–429; 205/783.5, 784, 784.5, 785

[56] References Cited

U.S. PATENT DOCUMENTS

| | | | |
|---|---|---|---|
| 3,816,269 | 6/1974 | Wilder | 204/422 |
| 3,980,543 | 9/1976 | Eckfeldt | 204/423 |
| 4,657,641 | 4/1987 | Nakamura et al. | 204/422 |
| 4,708,783 | 11/1987 | Nakamura et al. | 204/423 |

FOREIGN PATENT DOCUMENTS

| | | | |
|---|---|---|---|
| 073763 | 4/1984 | Japan | G01N 27/58 |
| 085361 | 5/1985 | Japan | C21C 5/46 |
| 113145 | 6/1985 | Japan | C21C 5/46 |

OTHER PUBLICATIONS

"Rapid determination of silicon activiities in hot metal by means of solid state electrochemical sensors equipped with an auxiliary electrode" (M. Iwase) Jun. 8, 1987.

"Development of electrochemical silicon sensors for iron and steel melts" (Klaus Raiber, Shi Wei Tu and Dieter Janke) Oct. 1990.

"Laboratory and In–Plant Tests of a Solid–State Silicon Sensor Incorporating a Mixture of $ZrO_2$ +$ZrSiO_4$ +$Na_2Si_2ZrO_7$ as an Auxiliary Electrode for Rapid Determination of Silicon Levels in Blast Furnace Hot Metal" (K. Gomyo and I. Sakaguchi, Y. Shin–ya and M. Iwase) Jul. 1991.

"Tri–phasic zirconia electrolyte for the in–situ determination of silicon activities in hot metal" (M. Iwase, Hiromitsu Abe and Hideki Iritani) 1988.

Three–Phase Zirconia Sensor for Rapid Determination of Silicon Levels in Hot Metal (K. Gomyo and I Sakaguchi, Y. Shin–ya, M. Iwase) Mar. 1993.

"Solid state sensor for silicon in molten metals by zirconia–based electrolyte" (K. Gomyo, I. Sakaguchi, Y. Sin–ya, V.I. Lakshmanan, A. McLean, M. Iwase) 1994.

"A New Silicon Sensor for Hot Metal Measurements" (K. Ichihara, D. Janke and Hans–Jurgen Engell) 1986.

"New electrochemical probe for silicon determination in hot metal" (Francesca Buiarelli and Paolo Granati) Feb. 1990.

"Mullite Silicon Sensor for Iron and Steel Melts" (R, Inoue and H. Suito) Apr. 1995.

Abstract of Japanese Patent Application (JP 63191056).

*Primary Examiner*—T. Tung
*Attorney, Agent, or Firm*—W. F. Riesmeyer, III

[57] ABSTRACT

A system is provided for measuring the concentration of an element in molten metal such as silicon, chromium, manganese or aluminum. The system includes a probe with a sensor having a solid electrolyte, a reference electrode in contact with a first surface of the electrolyte and an auxiliary electrode at a second surface thereof. The auxiliary electrode includes an oxide of the element to be measured and a metal-silicate selected from the group consisting of alkali metal-silicates, alkaline earth metal-silicates and mixtures thereof. The metal-silicate has a working point at about the temperature of the molten metal so as to form a viscous semi-molten mass adjacent the second surface of the electrolyte. The metal-silicate is capable of diffusing oxygen in the semi-molten state. Preferably the metal-silicate is in the form of a fibrous material so that it can be easily applied to the surface of the electrolyte.

16 Claims, 3 Drawing Sheets

FIG. 1
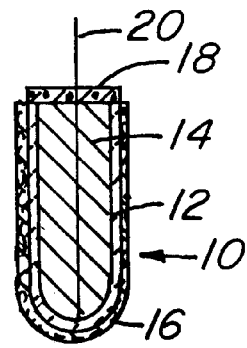
MEASURED emf AS A FUNCTION %Si IN HOT METAL
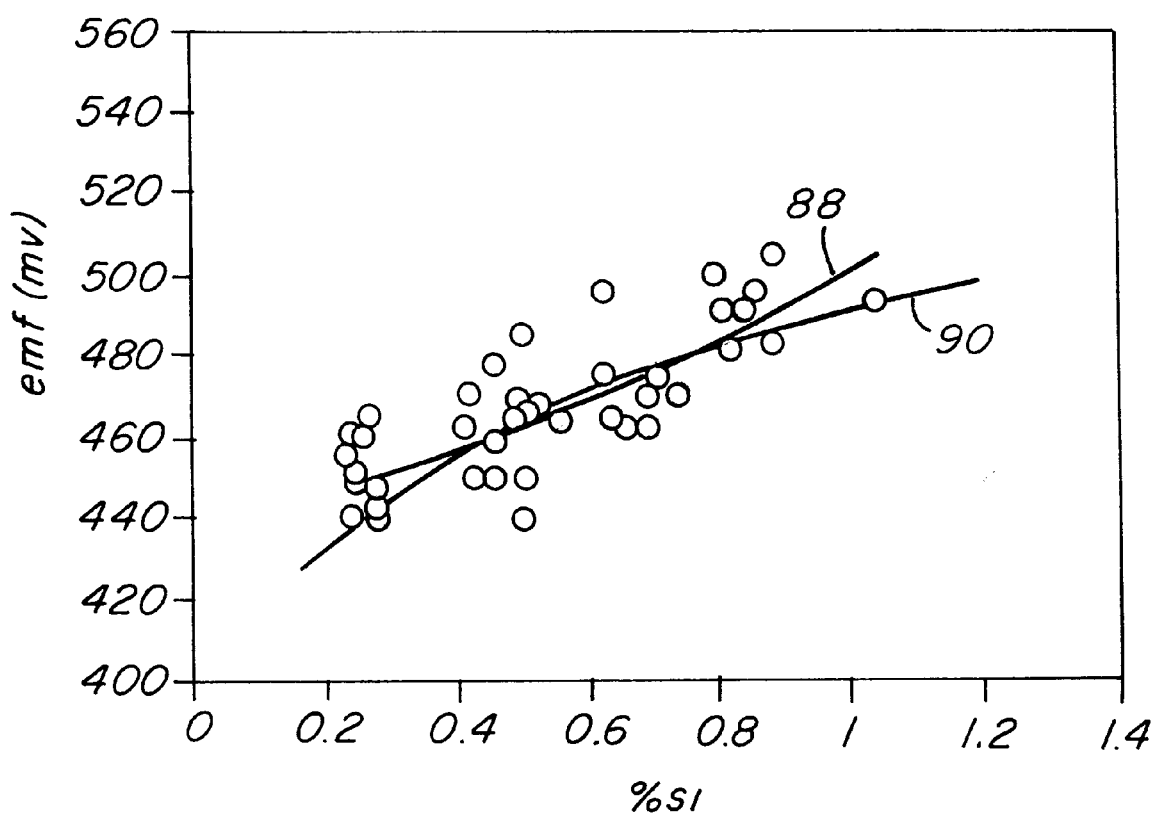
FIG. 5

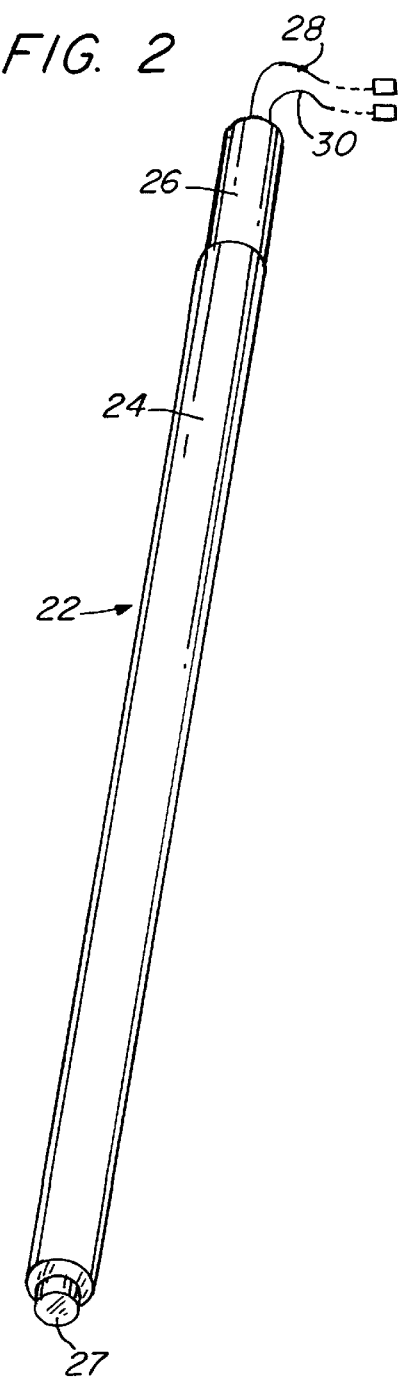
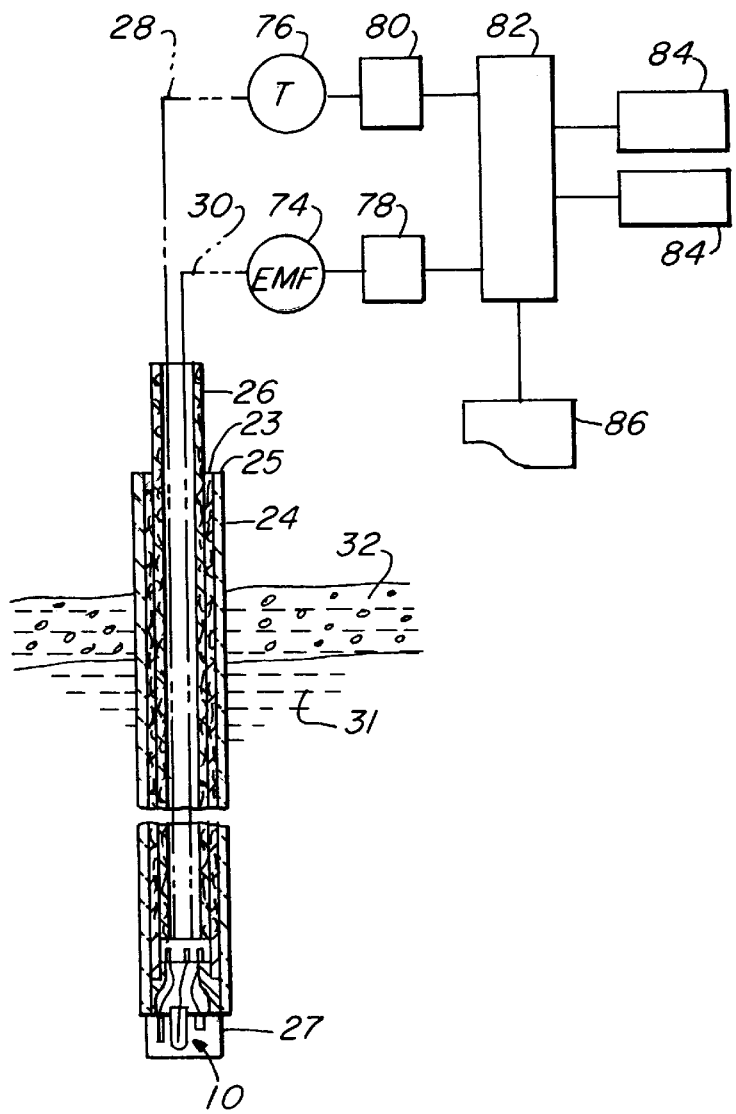
FIG. 2
FIG. 3

PROBE FOR DETECTION OF THE CONCENTRATION OF VARIOUS ELEMENTS IN MOLTEN METAL

TECHNICAL FIELD

This invention relates to a sensor for the detection of the concentration level of various elements in molten metal, and particularly to a sensor having an improved auxiliary electrode for the measurement of e.g. silicon, chromium, manganese or aluminum in a molten metal, and particularly for the measurement of such elements in molten iron or steel.

The auxiliary electrode includes a metal-silicate material which is adapted to have an oxide of the element to be measured physically mixed or chemically combined therein, said metal-silicate material having a "working point" such that it will fuse and form a viscous semi-molten mass upon immersion in the molten metal, said material being capable of diffusing oxygen in the semi-molten state and serving to retain the oxide of the element to be measured in close proximity with an electrolyte to which the auxiliary electrode has been applied, thus providing an emf across the electrolyte to a reference electrode as a measure of the concentration of the element in the molten metal.

BACKGROUND ART

Various sensors have been developed for measuring the silicon content of molten metal in situ, i.e. without sampling of the metal. One such device is described in U.S. Pat. Nos. 4,657,641 and 4,708,783. The sensor includes a solid electrolyte capable of conducting oxygen ions, a reference electrode in contact with one surface of the solid electrolyte for providing a constant oxygen potential at a particular temperature of measurement, and an auxiliary electrolyte comprising $SiO_2$ disposed in the immediate vicinity of the other surface of the solid electrolyte. The auxiliary electrolyte may consist of essentially pure silica. However, pure silica is said to be "not fully satisfactory, since it tends to be softened in the molten pig iron so that its surface configuration may be deformed owing to flows of the molten pig iron". The patents state preferably the auxiliary electrode is made of a compound, solution or mixture of $SiO_2$ with metallic oxides which are more stable than $SiO_2$ in the molten metal, such as Group IIA (alkaline earth), Group IA (alkali), Group IIIB and IVB of the Periodic Table. The auxiliary electrode may be in contact with the solid electrode or located in the immediate vicinity of the same. A porous auxiliary electrode is disclosed in FIGS. 7 and 8 of the patents. An auxiliary electrode consisting essentially of a two-phase mixture of $ZrO_2$ and $ZrSiO_4$ is most preferred. This auxiliary electrode is prepared by mixing particulate $ZrSiO_4$ and a paste of $ZrO_2$, coating the outer surface of the solid electrolyte with the paste mixture, and calcining the coating at a temperature of about 1300 to about 1500° C. The preferred form of the device is also described in a paper entitled "Rapid determination of silicon activities in hot metal by means of solid state electrochemical sensors equipped with an auxiliary electrode" by M. Iwase published in Scand. J. Metallurgy 17, (1988), pages 50–56. Variations of the aforementioned sensor are also disclosed in a paper entitled "Development of electrochemical silicon sensors for iron and steel melts" by K. Raiber, S. W. Tu and D. Janke, published in Steel Research 1990, pages 430–437. The latter paper discloses the use of one of the sensors for the measurement of chromium activities in Fe—O—Cr and Ni—O—Cr melts. A similar sensor using a multi-oxide auxiliary electrode comprising a mixture of $ZrO+ZrSiO_4+Na_2Si_2ZrO_7$ is disclosed in a paper entitled "Laboratory and In-Plant Tests of a Solid-State Silicon Sensor Incorporating a Mixture of $ZrO_2+ZrSiO_4+Na_2Si_2ZrO_7$ as an Auxiliary Electrode for Rapid Determination of Silicon Levels in Blast Furnace Hot Metal" by K. Gomyo, I Sakaguchi, Y. Shin-ya, and M. Iwase, published in Transactions of the ISS July, 1991, pages 71–78.

Other types of sensors are described below. One other sensor is described in a paper entitled "Tri-phasic zirconia electrolyte for the in-situ determination of silicon activities in hot metal" by M. Iwase, H. Abe and H. Iritani published in Steel Research 59 (1988) No. 10, pages 433–437. The sensor consists of an electrochemical cell with a tri-phasic zirconia electrolyte of cubic $ZrO_2$-MgO solid solution and monoclinic $ZrO_2$ and 2 $MgO.SiO_2$ and a reference electrode of $Mo+MoO_2$. The triphasic electrolyte is fabricated by mixing magnesia-stabilized zirconia and forsterite. This sensor is also described in two other papers: one entitled "Three-Phase Zirconia Sensor for Rapid Determination of Silicon Levels in Hot Metal" by K. Gomyo, I. Sakaguchi, Y. Shin-ya, and M. Iwase published in Transactions of the ISS March 1993, Pages 87–95 and another entitled "Solid state sensor for silicon in molten metals by zirconia-based electrolyte" by K. Gomyo, I. Sakaguchi, Y. Sin-ya, V. Lakshmanan, A. McLean and M. Iwase published in Solid State Ionics 1994 70/71, pages 551–554.

A sensor with a molten silicate electrolyte is described in a paper by K. Ichibara, D. Janke and H. J. Engell published in Steel Research 57 (1986) No. 4, Pages 166–171. Another sensor using a molten silicate electrolyte is described in a paper by F. Buiarelli and P. Granati entitled "New electrochemical probe for silicon determination in hot metal " published in Steel Research No. 2 1990, pages 60–63.

A sensor having a molten metal retention chamber is described in Japanese published application No. JP 63191056. A probe in which an ion-conductive silicate electrolyte is used is described in Japanese published application nos. JP 60113145, JP 60085361 and JP59073763.

Finally a sensor utilizing a mullite electrolyte and $Cr$—$Cr_2O_3$ reference electrode is described in a paper by R. Inoue and H. Suito published in Transactions of the ISS April 1995, pages 51–57.

Construction of the prior art sensors is fairly complicated and difficult. Also such sensors are not completely reliable or accurate and are somewhat costly.

SUMMARY OF THE INVENTION

The present invention is of an apparatus which is easy to manufacture and provides consistent electrochemical measurement of the concentration of an element, such as for example silicon, manganese, chromium or aluminum in molten metal, particularly in molten blast furnace iron (often referred to as hot metal), or molten steel. The apparatus comprises a sensor which includes a solid electrolyte capable of conducting oxygen ions, a reference electrode in contact with a first surface of the solid electrolyte for providing a constant oxygen potential at a particular temperature of measurement, and an auxiliary electrode mounted on a second surface of the solid electrolyte, said auxiliary electrode comprising an oxide of the element to be measured, for example $SiO_2$, MnO, $Cr_2O_3$ or $Al_2O_3$, and a metal-silicate material selected from the group consisting of alkali metal silicates, alkaline earth metal-silicates, and mixtures thereof, said metal-silicate material having a "working point" such that the metal-silicate material fuses and forms a viscous semi-molten mass at about the temperature of measurement, said metalsilicate material being capable of diffusing oxygen ions in the semi-molten state. Preferably the alkali metal-silicate is alkali aluminosilicate or alkali bororsilicate and the alkaline earth metal-silicate is alkaline aluminosilicate or alkaline borosilicate. It is also desirable that the metal-silicate is provided in the form of a fibrous material which can be applied easily to the surface of the electrolyte. The apparatus may also include a metallic electrode for making electrical contact with the reference electrode, a thermocouple for measuring the temperature of the molten metal, and a protective cap to envelope the sensor, metallic electrode and thermocouple, for protecting them upon immersion in the molten metal. The protective cap is composed of a consumable material which dissolves in the molten metal immediately after immersion in the molten metal without substantially changing the composition of the molten metal so that the sensor, metallic electrode and thermocouple become exposed to the molten metal. The apparatus may also include means for determining a potential difference between the reference electrode and metallic electrode exposed to the molten metal and for determining the temperature of the molten metal.

BRIEF DESCRIPTION OF THE DRAWINGS

FIG. 1 is a schematic cross-sectional view of a sensor according to the present invention.

FIG. 2 is a perspective view of a probe in which a sensor according to this invention is incorporated;

FIG. 3 is a schematic cross-sectional view of the measuring probe of FIG. 2, and also shows an arrangement of measuring instruments in a diagram;

FIG. 5 is a graph of % silicon in carbon-saturated iron versus emf in millivolts as measured using the sensor of this invention.

DESCRIPTION OF THE PREFERRED EMBODIMENT

Figure 4:
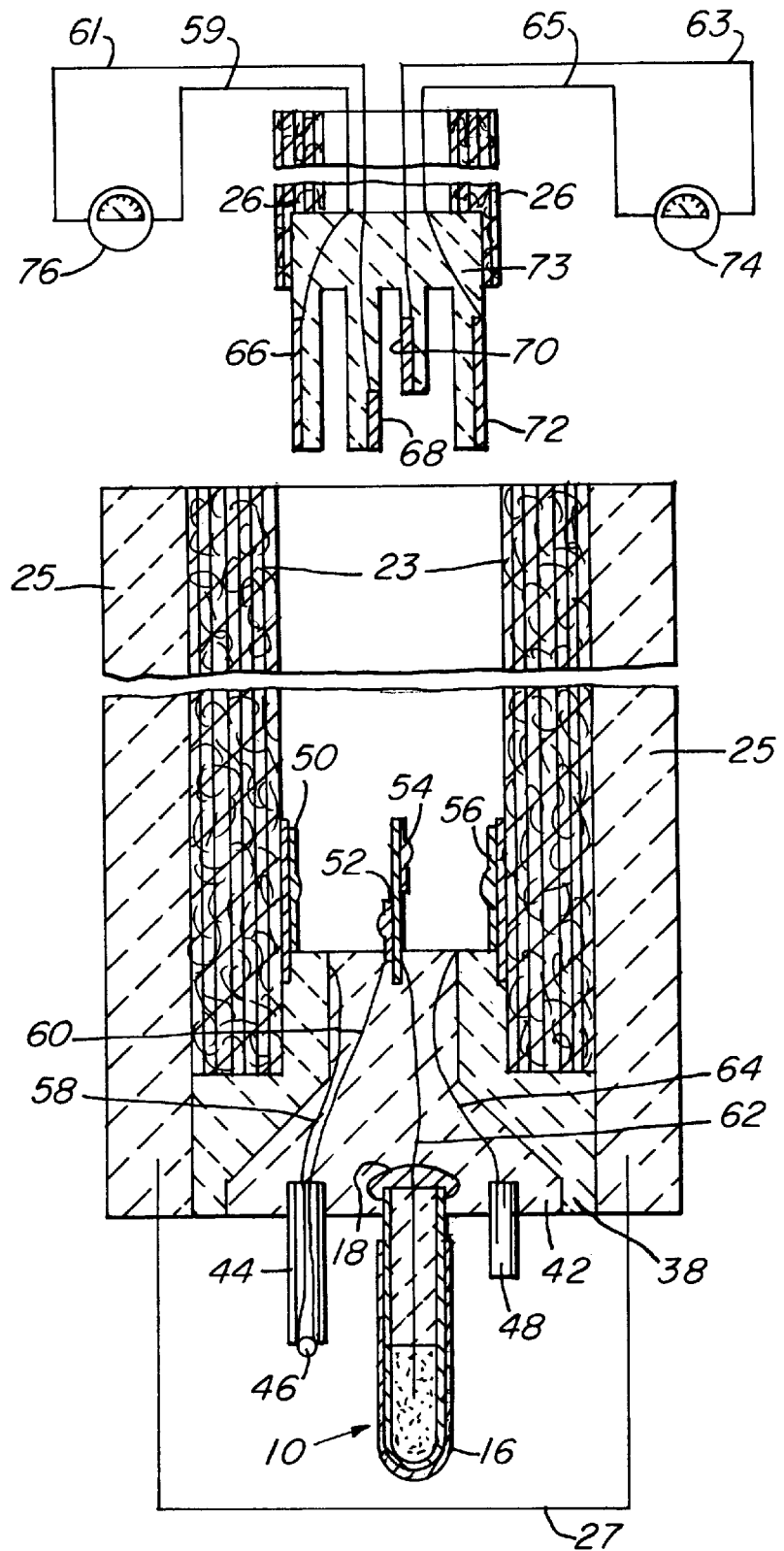
FIG. 4 is an enlarged cross-sectional view of the probe of FIGS. 2 and 3.

Referring to FIG. 1, according to this invention a sensor is provided for electro-chemically measuring the concentration of an element dissolved in molten metal, particularly including but not limited to the measurement of an element selected from the group consisting of silicon, chromium, manganese and aluminum in molten ferrous or non-ferrous metal, and especially for the measurement of those elements in molten blast furnace iron or hot metal, and steel. The sensor 10 comprises an electrolyte 12 which is capable of conducting oxygen ions and preferably is in the form of a refractory tube closed at one end. A reference electrode 14 is provided in the electrolyte tube in contact with a first surface thereof for providing a constant oxygen potential at a particular temperature of measurement. An auxiliary electrode 16 is provided at a second surface of the electrolyte tube for creating a region of substantially constant activity of an oxide of the element to be measured on said second surface. A cover of cement 18 is provided to seal the reference electrode in the electrolyte tube. A conductor 20 is provided preferably in the form of a metal wire or rod in contact with the reference electrode.

Preferably the electrolyte 12 is of a material which comprises a partially stabilized $ZrO_2$ which has been commonly used in commercial oxygen sensors. Such zirconia electrolytes generally contain from about 3 to about 10 weight percent CaO or MgO. The reference electrode 14 may comprise a solid reactive mixture, a reactive gas mixture or a non reactive gas as is well known in the art. Preferably reference electrode 14 is a reactive solid mixture such as particulate $Cr/Cr_2O_3$, Ni/NiO or $Mo/MoO_2$. The conductor 20 is an electrically conductive metal material, preferably molybdenum.

According to this invention, the auxiliary electrode 16 comprises an oxide of the element to be measured e.g. $SiO_2$ where the concentration of silicon is to be measured, and a metal-silicate material selected from the group consisting of alkali metal-silicate, alkaline earth metal-silicate, and mixtures thereof, said metal-silicate material having a "working point" at a temperature such that the metal-silicate forms a viscous semi-molten mass on a second surface of the electrolyte at the temperature of measurement. The metal-silicate should also be selected so as to be able to diffuse oxygen readily in the semi-molten state. Preferably the metal-silicate is selected from the group consisting of alkali aluminosilicate, alkaline aluminosilicate, alkali borosilicate and alkaline borosilicate. Most preferably the metal-silicate is in the form of a fibrous material which can be readily applied to the surface of the electrolyte. The oxide e.g. $SiO_2$ may be included as a chemical component in the metal-silicate material itself, or it may be applied in particulate form either to the fibrous metal-silicate material or to the surface of the electrolyte after first using an organic wetting agent such as methanol to cause the particles to stick to the electrolyte surface. The fibrous metal-silicate material is then applied to the electrolyte surface and may be partially fused by passing a gas flame across its surface to secure it in place. Alternatively the fibrous material containing the oxide may be wrapped onto a blank tube followed by passing a gas flame across its outer surface to partially melt it, thus forming a "cocoon" which can be removed and fitted onto the electrolyte tube.

Referring to FIGS. 2 and 3, a probe 22 is shown for dipping the sensor into molten metal. The probe comprises elongated hollow cylindrical members 24 and 26 that fit together in socket and plug relation and define first and second probe elements. Cynlindrcal member 24 preferably comprises a coiled paper tube 23 (FIG. 3) with an outer refractory coating 25. Cylindrical member 26 may also be of coiled paper construction. A protective cap 27 encloses sensor 10 (FIG. 3) and extends longitudinally from one end of the probe and two pairs of conducting wires 28 and 30 extend from the other end. The conducting wires are connected to a potentiometer and a thermoelectric thermometer, respectively as described hereafter. Upon measurement the probe is partially immersed into a molten metal such as carbon-saturated blast furnace iron or hot metal, or steel. The molten metal 31 may be covered with a slag layer 32 as shown in FIG. 3. To prevent contamination of the sensor by the slag layer, protective metal cap 27 is preferably made of the same metal as the molten metal 31 in which the measurement is to be taken. The cap melts away immediately after the probe has been dipped through the slag layer when the sensor is in a position for measurement.

The internal structure of the probe is shown in FIG. 4 and preferably includes a ceramic housing 38 mounted at one end of coiled paper tube 23. A cavity in the ceramic housing is filled with refractory cement 42. Sensor 10 projects downwardly from the housing along with a thermocouple tube 44 having a thermocouple 46 therein, and a metal electrode 48, which is preferably a molybdenum rod. Metal cap 27 covers the lower end of the sensor, thermocouple tube and metal electrode. An electrical circuit is provided including means for determining a potential difference between said reference electrode and the metal electrode exposed to the molten metal and the temperature of the molten metal. Socket contacts 50, 52, 54 and 56 are provided which have lead lines 58, 60, 62, and 64 connected to them. Lead lines 58 and 60 are contacts to the thermocouple 46 and to socket contacts 50 and 52. Lead line 62 extends to the reference electrode 14 and is connected to socket contacts 54, whereas lead line 64 is connected to metal electrode 48 and to socket contact 56. Cylindrical member 26 has plug contacts 66, 68, 70 and 72 adapted to receive corresponding socket contacts of cylindrical member 24. Socket contacts 50 and 52 engage plug contacts 66 and 68, respectively. Similarly socket contacts 54 and 56 engage plug contacts 70 and 72, respectively. Lead lines 59 and 61 extend from plug contacts 66 and 68 to thermoelectric thermometer 76 (FIGS. 3 and 4). Lead lines 63 and 65 extend from plug contacts 70 and 72 to potentiometer 74 (FIGS. 3 and 4). An arrangement of instruments for reading the concentration of the element to be measured in the molten metal from electro-motive force signals detected by the sensor is shown in FIG. 3. Analog to digital converters 78 and 80 are connected to the potentiometer 74 and thermometer 76 for converting two series of electrical signals form the sensor to digital signals which are directed to a micro computer 82 where the input values are converted to the concentration of the element according to conversion formulas. The values are then sent to a display 84 and a printer 86.

FIG. 5 shows a plot of emf versus silicon content detected in laboratory tests by a silicon sensor according to the invention in molten hot metal or carbon-saturated iron. The sensor for these laboratory tests was constructed a follows: An electrolyte tube closed at one end and composed of a 7 mole percent MgO-stabilized ZrO2 was packed with a mixture of reagent grade particulate Mo and $MoO_2$. The tube measured 5 mm OD, 3 mm ID and 30 mm in length. $Al_2O_3$ powder was packed on top of the Mo, $MoO_2$ mixture. A molybdenum wire was inserted into the tube extending down into the Mo and $MoO_2$ mixture. The top of the materials in the tube were sealed in place with $ZrO_2$ cement. An auxiliary electrode was then prepared for application to the outer surface of the electrolyte tube. We used Pyrex brand glass wool manufactured by Corning, Inc. of Corning, New York and sprinkled $SiO_2$ powder on a thin bed of the glass wool. The glass wool was then wrapped onto a "blank" $ZrO_2$ tube of the same size as the electrolyte tube. A gas torch was used to melt the outer layer of the glass wool slightly and form it into shape. The $SiO_2$ glass wool mixture was then removed from the blank tube and placed on the $ZrO_2$ tube filled with Mo and $MoO_2$. A quartz tube was then placed in surrounding relation to the electrolyte tube and cemented in place. The sensor was then used to take measurements of the silicon content of carbon-saturated iron melted in an induction furnace. The silicon content of the metal was varied by adding FeSi alloy to the melt. Samples were obtained from the melt and separately analyzed as a check on the amount of silicon in the metal. The emf values obtained were corrected for the thermal emf of the molybdenum electrode by subtracting 20 millivolts from each reading. The results plotted in FIG. 5 show a close correlation between a best fit curve 88 (where $R^2$=0.66) with theoretical predictions illustrated by curve 90. Thus, a sensor is provided which is easy to manufacture and gives accurate readings of the concentration of silicon and other elements in molten metal.

We claim:

1. A sensor for use in a system for obtaining consistent in-situ electro-chemical measurements of the concentration of an element dissolved in molten iron-base metal, said sensor comprising:

a solid electrolyte capable of conducting oxygen ions, a reference electrode in contact with a first surface of the electrolyte for providing a constant oxygen potential at a particular temperature, and an auxiliary electrode at a second surface of the electrolyte comprising an oxide of the element to be measured and a metal-silicate material selected from the group consisting of alkali aluminosilicate, alkaline aluminosilicate, alkali borosilicate, alkaline borosilicate and mixtures thereof, said metal-silicate material having a working point so as to form a viscous semi-molten mass on said second surface of the electrolyte at the temperature of measurement, said metal-silicate also being capable of diffusing oxygen in the semi-molten state.

2. The sensor of claim 1 wherein said metal-silicate comprises a fibrous material.

3. The sensor of claim 2 wherein the fibers of said fibrous metal-silicate material are comprised of said metal-silicate and the oxide of the element to be measured.

4. The sensor of claim 2 wherein the oxide of the element to be measured is physically mixed into the fibers of the fibrous metal-silicate material.

5. The sensor of claim 1 wherein the element to be measured is selected from the group consisting of silicon, chromium, manganese and aluminum and the oxide in said auxiliary electrode comprises $SiO_2$, $Cr_2O_3$, MnO or $Al_2O_3$, respectively.

6. A probe element for use in a system for obtaining consistent in-situ electro-chemical measurements of the concentration of an element dissolved in molten iron-base metal, said probe element comprising:

an elongated hollow cylindrical member, a housing mounted in one end of the elongated hollow cylindrical member, a metallic electrode, a thermocouple and a sensor mounted at spaced locations in said housing and protruding therefrom outwardly of said elongated hollow cylindrical member;

a protective cap enveloping the sensor, the metallic electrode and the thermocouple, for protecting them upon their immersion in the molten metal, said cap being composed of a consumable material which dissolves immediately after the immersion in the molten metal without substantially changing the composition of the molten metal so that said sensor, metallic electrode and thermocouple may be exposed to the molten metal;

said sensor including a solid electrolyte capable of conducting oxygen ions, a reference electrode in contact with a first surface of the electrolyte for providing a constant oxygen potential at a particular temperature, and an auxiliary electrode at a second surface of the electrolyte comprising an oxide of the element to be measured and a metal-silicate material selected from the group consisting of alkali aluminosilicate, alkaline aluminosilicate, alkali borosilicate, alkaline borosilicate, and mixtures thereof, said metal-silicate material having a working point so as to form a viscous semi-molten mass on said second surface of the electrolyte at the temperature of measurement, said metal-silicate also being capable of diffusing oxygen in the semi-molten state, a plurality of electrical contacts adjacent an opposite end of the elongated cylindrical member, and electrical conductors extending from said thermocouple, the reference electrode and said metal electrode respectively to said electrical contacts, said electrical contacts being adapted for contact with electrical contacts of a second probe element of said system.

7. The probe element of claim 6 wherein said metal-silicate comprises a fibrous material.

8. The probe element of claim 7 wherein the fibers of said fibrous metal-silicate material are comprised of said metal-silicate and the oxide of the element to be measured.

9. The probe element of claim 7 wherein the oxide of the element to be measured is physically mixed into the fibers of the fibrous metal-silicate material.

10. The probe element of claim 6 wherein the element to be measured is selected from the group consisting of silicon, chromium, manganese and aluminum and the oxide in said auxiliary electrode comprises $SiO_2$, $Cr_2O_3$, $MnO$ or $Al_2O_3$, respectively.

11. A system for obtaining consistent in-situ electrochemical measurements of the concentration of an element dissolved in molten iron-base metal, said system comprising:

first and second hollow elongated cylindrical probe elements which fit together end-to-end in socket and plug relation, said first probe element including a housing mounted in one end thereof, a metallic electrode, a thermocouple and a sensor mounted at spaced locations in said housing and protruding therefrom outwardly of said elongated hollow cylindrical member;

a protective cap enveloping the sensor, the metallic electrode and the thermocouple, for protecting them upon their immersion in the molten metal, said cap being composed of a consumable material which dissolves immediately after the immersion in the molten metal without substantially changing the composition of the molten metal so that said sensor, metallic electrode and thermocouple may be exposed to the molten metal;

and sensor including a solid electrolyte capable of conducting oxygen ions, a reference electrode in contact with a first surface of the electrolyte for providing a constant oxygen potential at a particular temperature, and an auxiliary electrode at a second surface of the electrolyte comprising an oxide of the element to be measured and a metal-silicate material selected from the group consisting of alkali aluminosilicate, alkaline aluminosilicate, alkali borosilicate, alkaline borosilicate, and mixtures thereof, said metal-silicate material having a working point so as to form a viscous semi-molten mass on said second surface of the electrolyte at the temperature of measurement, said metal-silicate also being capable of diffusing oxygen in the semi-molten state, a plurality of electrical contacts adjacent an opposite end of said first probe element, electrical conductors extending from said thermocouple, the reference electrode and said metal electrode respectively to said electrical contacts, the second probe element including electrical contacts adjacent one end thereof for contact with the electrical contacts of the first probe element and electrical conductors extending from said contacts, and an electrical circuit connected to said electrical conductors including a potentiometer for determining a potential difference between said reference electrode and the metal electrode exposed to the molten metal and a thermoelectric thermometer connected to said thermocouple for determining the temperature of the molten metal.

12. The system of claim 11 wherein said metal-silicate comprises a fibrous material.

13. The system of claim 12 wherein the fibers of said fibrous metal-silicate material are comprised of said metal-silicate and the oxide of the element to be measured.

14. The system of claim 12 wherein the oxide of the element to be measured is physically mixed into the fibers of the fibrous metal-silicate material.

15. The system of claim 11 wherein the element to be measured is selected from the group consisting of silicon, chromium, manganese and aluminum and the oxide in said auxiliary electrode comprises $SiO_2$, $Cr_2O_3$, $MnO$ or $Al_2O_3$, respectively.

16. A system for obtaining consistent in-situ electrochemical measurements of the concentration of an element dissolved in molten iron-base metal, said system comprising:

an elongated hollow cylindrical probe element including a housing mounted in one end thereof, a metallic electrode, a thermocouple and a sensor mounted at spaced locations in said housing and protruding therefrom outwardly of said probe;

a protective cap enveloping the sensor, the metallic electrode and the thermocouple, for protecting them upon their immersion in the molten metal, said cap being composed of a consumable material which dissolves immediately after the immersion in the molten metal without substantially changing the composition of the molten metal so that said sensor, metallic electrode and thermocouple may be exposed to the molten metal;

said sensor including a solid electrolyte capable of conducting oxygen ions, a reference electrode in contact with a first surface of the electrolyte for providing a constant oxygen potential at a particular temperature, and an auxiliary electrode at a second surface of the electrolyte comprising an oxide of the element to be measured and a metal-silicate material selected from the group consisting of alkali aluminosilicate, alkaline aluminosilicate, alkali borosilicate, alkaline borosilicate, and mixtures thereof, said metal-silicate material having a working point so as to form a viscous semi-molten mass on said second surface of the electrolyte at the temperature of measurement, said metal-silicate also being capable of diffusing oxygen in the semi-molten state, and electrical circuit means for determining the potential difference between said reference electrode and the metal electrode exposed to the molten metal and for determining the temperature of the molten metal.

* * * * *